United States Patent [19]

Shimanaka

[11] Patent Number: 4,576,671
[45] Date of Patent: Mar. 18, 1986

[54] METHOD OF MANUFACTURING ALATE MEDICAL NEEDLE

[76] Inventor: Hirotaka Shimanaka, 3-8-19, Sakurao, Hatsukaichi-cho, Saeki-gun, Hiroshima-pref., Japan

[21] Appl. No.: 626,612

[22] Filed: Jun. 29, 1984

[30] Foreign Application Priority Data

Jul. 6, 1983 [JP] Japan ............................ 58-123646
Oct. 31, 1983 [JP] Japan ............................ 58-205571
Oct. 31, 1983 [JP] Japan ............................ 58-205572

[51] Int. Cl.$^4$ ............................................. B29C 65/04
[52] U.S. Cl. .............................. 156/245; 156/272.2; 156/273.9; 156/274.4; 264/26; 264/27; 264/248; 604/177
[58] Field of Search ............... 156/311, 321, 322, 213, 156/272.2, 309.9, 245, 273.9, 274.4; 264/25, 249, 26, 248, 320, 27; 604/177

[56] References Cited

U.S. PATENT DOCUMENTS

| | | | |
|---|---|---|---|
| 2,282,168 | 5/1942 | Cunnington | 156/213 |
| 2,914,181 | 11/1959 | Naftulin et al. | 264/27 |
| 3,064,648 | 11/1962 | Bujan | 604/177 |
| 3,454,442 | 7/1969 | Heller | 156/322 |
| 4,015,600 | 4/1977 | Liautaud | 604/177 |
| 4,192,304 | 3/1980 | Millet | 604/177 |

Primary Examiner—Willard E. Hoag
Attorney, Agent, or Firm—Barry Kramer; Frederick H. Rabin

[57] ABSTRACT

This invention relates to an improvement in the method of manufacturing alate medical needles. The base part of a needle is inserted into a thermoplastic resin tube and the inserted portion is set in a wing-forming mold. The thermoplastic resin is heated to mold wings integral with the tube. Since the molding of the wings and their connection to the tube can be accomplished simultaneously, this method enables high-speed continuous manufacture which is impossible with conventional methods. Heating of the thermoplastic resin is preferably conducted by high-frequency dielectric heating.

3 Claims, 4 Drawing Figures

METHOD OF MANUFACTURING ALATE MEDICAL NEEDLE

BACKGROUND OF THE INVENTION

This invention relates to a method for manufacturing an alate medical needle, and more particularly, to a method of manufacturing such needles by a simple process which enables high-speed production.

Alate needles are conventionally used for the infusion or the extracorporeal circulation of blood, and for other purposes. An alate needle usually consists of a needle, wings attached to the base of the needle, and a tube. The following two types of methods are generally employed for manufacture of such needles. In one method, the wings are formed by injection molding of a thermoplastic resin, and the needle, molded wings, and tube are bonded together with an appropriate bonding agent. In the other method, the needle is inserted into a mold in an injection molding step so that the wings are molded while being simultaneously secured to the needle. Then, a tube is bonded thereto with a bonding agent. These methods, however, are disadvantageous for high-speed continuous manufacture because they both include an injection molding step. Injection molding usually requires a cycle time of at least 20 seconds, and when an injection molding step is included as an essential part of the manufacturing process, full automation of the whole process is difficult because it is difficult to automate the combination of such injection molding step with other steps. The bonding step required in these methods makes the process more complicated and time-consuming. Thus, conventional methods are incapable of high-speed continuous production and limit any reduction of the manufacturing cost. Heavy equipment investment is required for the injection molding, and this adds to the economic disadvantage of conventional methods.

SUMMARY OF THE INVENTION

An object of this invention is to provide a method which enables the high-speed, continuous production of alate needles.

Another object of this invention is to provide a method which can produce alate needles at a low cost.

The present invention provides a method of manufacturing an alate needle consisting of a needle, wings, and a tube, which method comprises inserting the base part of a needle into a thermoplastic resin tube, placing the inserted portion in a wing-forming mold, and then heating the thermoplastic resin in the mold to form the wings while integrally securing them to the tube. In this invention, the heating of the resin is preferably done by high-frequency dielectric heating. High-frequency dielectric heating is a method of heating a material by making use of the phenomenon that a material, when placed in a high-frequency electric field, is heated by dielectric losses.

BRIEF DESCRIPTION OF DRAWINGS

Other objects and advantages of this invention will become apparent from the following description together with the accompanying drawings, in which.

DETAILED DESCRIPTION OF THE INVENTION

Figure 1:
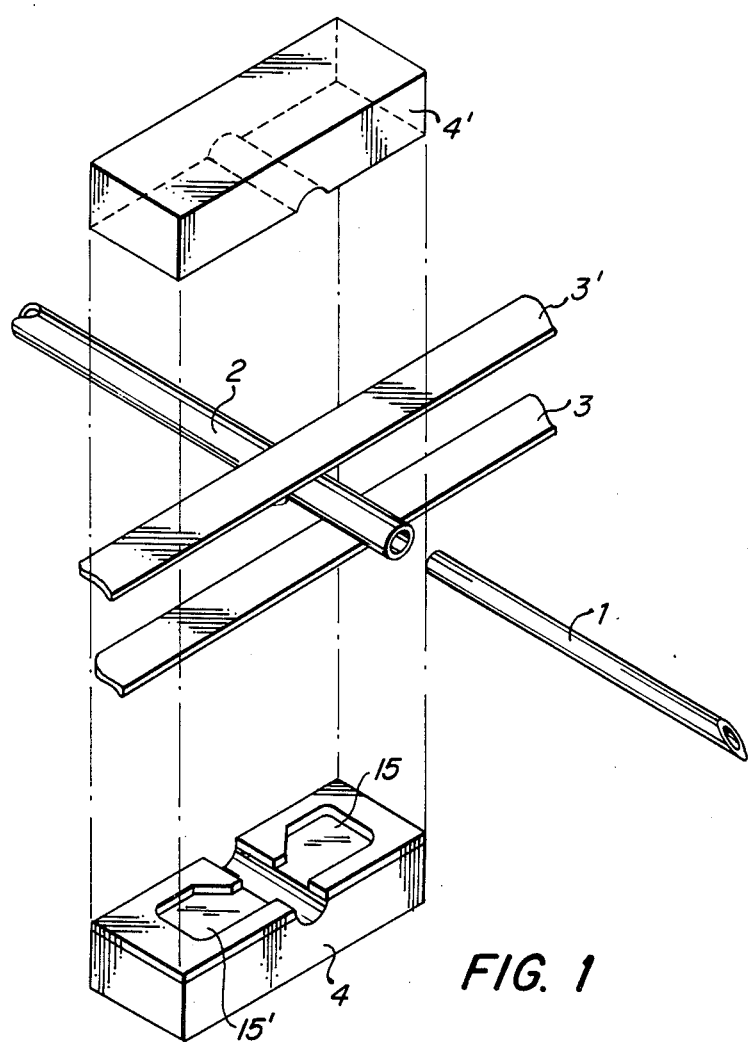
FIG. 1 is a perspective view of the materials and mold necessary for applying the method of this invention.
Figure 2:
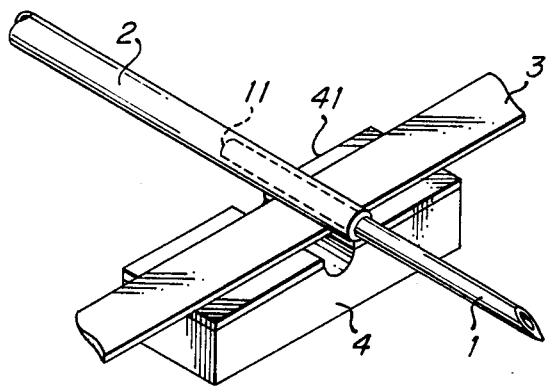
FIG. 2 is a perspective view of a preferred positional relation between the mold and the materials.

FIG. 1 is a perspective view of a needle, a tube, a wing-forming material, and a mold of one embodiment of the method of this invention before molding. The base part of the needle 1 is inserted into the tube 2. A pair of thermoplastic resin sheets 3 and 3', from which the wings are to be formed, are placed on either side of the tube 2 and are held by mold segments 4, 4'. The mold segments contain wing-shaped indentations 15 and 15'. FIG. 2 shows one positional arrangement of the needle 1, tube 2, sheet 3 and mold segment 4 just before the molding, with sheet 3 covering the indentations 15 and 15' (not visible). The sheet 3' and mold segment 4' are not shown. An end 11 of the inserted base part of the needle 1 is preferably positioned outside a side surface 41 of the mold 4, as shown in FIG. 2. This arrangement can prevent deformation or blockage of the tube when it is heated, and enables the stable formation of good products. The distance between the end 11 of the needle base part and the side surface 41 of the mold is preferably between about 0.5 to 10 mm.

Figure 3:
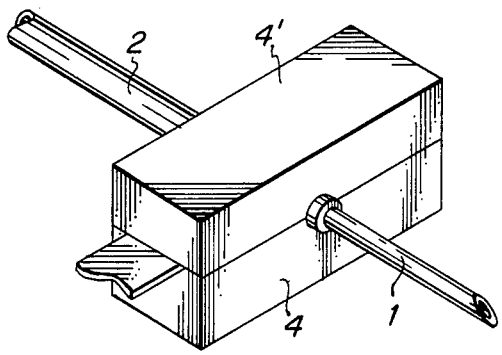
FIG. 3 is a perspective view of the molding operation.

The needle 1, tube 2, and sheets 3 and 3' are sandwiched between the mold segments 4 and 4', and then the sheets are heated to soften or fuse them and mold wings which are simultaneously integrated with the tube. FIG. 3 shows the sheets being heated in the mold. Heating of the sheets may be accomplished by heating the mold by an electrical means, or by using a heating medium, but high-frequency dielectric heating is preferred because this heating method is simple in operation and is convenient for high-speed processing. In the above embodiment, this high-frequency dielectric heating can be achieved by passing a high-frequency current through the mold, using its two segments as positive and negative electrodes. Upon application of a high-frequency current, the sheets and the tube are heated by dielectric losses and softened or fused to form the wings which are simultaneously integrated with the tube. In this invention, it is also possible to use a method in which a tube in which a needle is inserted is placed in a mold, and molten resin is injected into the mold to form the wings.

Figure 4:
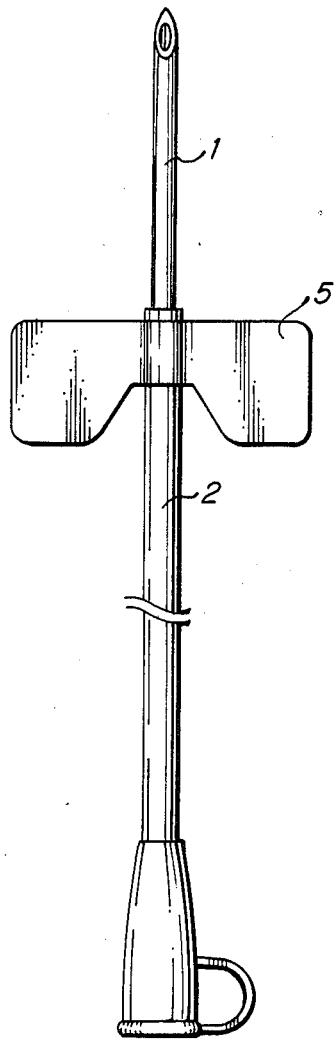
FIG. 4 is a front view of an alate needle manufactured according to the method of this invention.

The needle 1 and tube 2 are secured to each other to a satisfactory degree by this operation; but for a more positive attachment, it is advisable to bond them together with a bonding agent, or by heat and pressure bonding. It is especially preferable to heat and pressure bond the tube and needle together by high-frequency dielectric heating, using the needle 1 as one electrode and the mold as another electrode, either immediately before or after or concurrently with the formation of the wings, as this operation can simplify the production process and increase productivity, and is also advantageous economically. FIG. 4 is an example of an alate needle obtained in this way.

In the above embodiment, two sheets of thermoplastic resin were used as the wing-forming material, but it is possible to use just one sheet, and the material can have a shape other than a sheet. It is also possible to use liquid resin which can be solidified by heating. The thermoplastic resin used in this invention is not subject to any specific restrictions, but when employing high-frequency dielectric heating, it is recommended to use a resin which provides a large dielectric loss, such as polyvinyl chloride, methacrylate polymers, nylon, ABS resin, and the like. It is, however, possible to use a resin which provides a small dielectric loss by blending it with a material which provides a large dielectric loss. Of these resins, polyvinyl chloride is the most preferred because of its good workability and economic advantages. A preferred example of the liquid resin is a polyvinyl chloride paste resin. The material of the tube is also preferably selected from these substances.

The base part of the needle used for this invention may be provided with a surface coating, surface roughening, indentations, or other processing to facilitate its secure attachment to the tube. The mold may be either of a type which can produce a single alate needle per run, or of the type which can produce two or more alate needles at a time.

According to this invention, the joining of the wings and the tube can be done simultaneously with the formation of the wings, so that the process is simpler than conventional methods. If high-frequency heating is used for the molding of the wings, the molding cycle can be shortened to enable high-speed production. If high-frequency heating is employed for both the molding of the wings and the positive connection of the needle and tube, the steps of bonding with a bonding agent and the injection molding can be eliminated and hence the process is further simplified, which increases the effects of this invention in high-speed operation and manufacturing cost reduction. This also enables the full automation of the whole process, and provides an additional economic advantage.

The method of this invention can be applied to the production of various types of alate needles used in the medical field, but is especially useful for the manufacture of scalp vein infusion sets.

Although the invention has been described in a preferred embodiment with a certain degree of specificity, it must be understood that the details of the construction and the combination and arrangement of parts of this embodiment may be modified by those skilled in the art without departing from the spirit and the scope of the invention as hereinafter claimed.

What is claimed is:

1. A method of manufacturing an alate needle comprising a needle, wings, and a tube, which method comprises inserting a base portion of a needle into a thermoplastic resin tube, placing the inserted portion of said tube and one or two sheets of thermoplastic resin into a wing-forming mold, the tube being positioned so that the base portion of the needle lies outward of a side surface of the mold, and heating the thermoplastic resin by using the mold and the needle as electrodes and passing a high-frequency current there through, thereby simultaneously bonding the needle and tube together and forming wings which are integral with said tube.

2. The method of manufacturing an alate needle as set forth in claim 1, wherein two sheets of thermoplastic resin are used and said sheets are placed on either side of said tube.

3. The method of manufacturing an alate needle as set forth in claim 1 wherein said thermoplastic resin is polyvinyl chloride.

* * * * *

UNITED STATES PATENT AND TRADEMARK OFFICE
CERTIFICATE OF CORRECTION

PATENT NO. : 4,576,671

DATED : March 18, 1986

INVENTOR(S) : Hirotaka Shimanaka

It is certified that error appears in the above-identified patent and that said Letters Patent is hereby corrected as shown below:

On the title page, insert:

Assignee: Japan Medical Supply Co., Ltd
Hiroshima, Japan

Signed and Sealed this

Fifteenth Day of September, 1987

Attest:

DONALD J. QUIGG

Attesting Officer

Commissioner of Patents and Trademarks